(12) United States Patent
Yu et al.

(10) Patent No.: US 10,172,796 B2
(45) Date of Patent: Jan. 8, 2019

(54) USE OF UMIROLIMUS AND ITS DERIVATIVES FOR TREATING CANCER

(71) Applicant: Manli International Ltd., Singapore (SG)

(72) Inventors: Ting-Bin Yu, Irvine, CA (US); Shih-Horng Su, Irvine, CA (US)

(73) Assignee: Manli International Ltd., Singapore (SG)

( * ) Notice: Subject to any disclaimer, the term of this patent is extended or adjusted under 35 U.S.C. 154(b) by 828 days.

(21) Appl. No.: 14/093,876

(22) Filed: Dec. 2, 2013

(65) Prior Publication Data
US 2014/0154305 A1 Jun. 5, 2014

Related U.S. Application Data

(60) Provisional application No. 61/732,629, filed on Dec. 3, 2012.

(51) Int. Cl.
| A61K 9/107 | (2006.01) |
| A61K 9/127 | (2006.01) |
| A61K 9/00 | (2006.01) |
| A61K 31/436 | (2006.01) |

(52) U.S. Cl.
CPC .......... *A61K 9/1273* (2013.01); *A61K 9/0019* (2013.01); *A61K 9/107* (2013.01); *A61K 9/1075* (2013.01); *A61K 9/1271* (2013.01); *A61K 31/436* (2013.01)

(58) Field of Classification Search
CPC ................................. A61K 9/51; A61K 9/5146
See application file for complete search history.

(56) References Cited

U.S. PATENT DOCUMENTS

| 4,885,171 | A | 12/1989 | Surendra et al. |
| 7,220,755 | B2 | 5/2007 | Betts et al. |
| 8,012,508 | B2 | 9/2011 | Ludwig |
| 2004/0138095 | A1* | 7/2004 | Soula ............... A61K 9/5146 514/5.9 |
| 2005/0131008 | A1 | 6/2005 | Betts et al. |
| 2006/0198867 | A1 | 9/2006 | Toner et al. |
| 2006/0251710 | A1 | 11/2006 | Kwon et al. |
| 2009/0149511 | A1 | 6/2009 | Burk et al. |
| 2011/0076308 | A1 | 3/2011 | Kwon et al. |
| 2011/0166547 | A1* | 7/2011 | Baumbach ............ A61K 31/00 604/509 |

(Continued)

FOREIGN PATENT DOCUMENTS

| JP | H06/107565 A | 4/1994 |
| JP | H09/208494 A | 8/1997 |

(Continued)

OTHER PUBLICATIONS

Holowka, E.P., et al, in J. Am. Chem. Soc. 2005, vol. 127, pp. 12423-12428.*

(Continued)

*Primary Examiner* — Gollamudi Kishore
(74) *Attorney, Agent, or Firm* — Cesari and McKenna, LLP (57) ABSTRACT

Novel encapsulated umirolimus and umirolimus polymer conjugate formulations having enhanced permeability and retention at tumor sites. Also provided are methods for treating cancer by administering the umirolimus formulations.

3 Claims, 3 Drawing Sheets

(56) References Cited

U.S. PATENT DOCUMENTS

| | | |
|---|---|---|
| 2011/0189092 A1 | 8/2011 | Eliasof et al. |
| 2011/0200556 A1 | 8/2011 | Gutkind et al. |
| 2012/0064124 A1 | 3/2012 | McClain et al. |
| 2012/0196870 A1 | 8/2012 | Arbiser |
| 2012/0276169 A1 | 11/2012 | Kang et al. |

FOREIGN PATENT DOCUMENTS

| | | |
|---|---|---|
| JP | 2003/532688 A | 11/2003 |
| JP | 2007/533647 A | 11/2007 |
| JP | 2009/240954 A | 10/2009 |
| JP | 2010/536554 A | 12/2010 |
| WO | WO-2009/058895 A1 | 5/2009 |
| WO | WO-2010/022243 A1 | 2/2010 |
| WO | WO-2011/024168 A2 | 3/2011 |
| WO | WO-2011/053938 A1 | 5/2011 |
| WO | WO-2011/082367 A2 | 7/2011 |
| WO | WO-2011/133668 A2 | 10/2011 |
| WO | WO-2012/034079 A2 | 3/2012 |

OTHER PUBLICATIONS

Alavi et al "In Vitro Evaluation of the Efficacy of Liposomal and Pegylated Liposomal Hydroxyurea" Ind J Clin Biochem, vol. 29, pp. 84-88. 2014.

Cho et al "Polymeric Micelles for Neoadjuvant Cancer Therapy and Tumor-Primed Optical Imaging" American Cancer Society Nano vol. 5, pp. 1-14, 2011.

Wang et al "Preparation of Tacrolimus Loaded Micelles Based on Poly(ε-Caprolactone)-Poly(Ethylene Glycol)-Poly(ε-Caprolactone)" International Journal of Pharmaceutics vol. 407, pp. 184-189. 2011.

Miller et al "Comparative Investigations on In Vitro Serum Stability of Polymeric Micelle Formulations" Pharmaceutical Research vol. 29, pp. 448-459. 2012.

Bawarski, Willie E., et al., "Emerging Nanopharmaceuticals," Elsevier, Inc., ScienceDirect, Nanomedicine: Nanotechnology, Biology, and Medecine, vol. 4, 2008, pp. 273-282.

Blanco, Elvin, et al., "Multifunctional Miceller Nanomedicine for Cancer Technology," Minireview, The Society for Experimental Biology and Mediceine, 2009, pp. 123-131.

Duncan, Ruth, "Development of HPMA Copolymer-anticancer Conjugates: Clinical Experience and Lessons Learnt," Elsevier B.V., Advanced Drug Delivery Reviews, vol. 61, 2009, pp. 1131-1148.

Duncan, Ruth, "The Dawning Era of Polymer Therapeutics," Nature Publishing Group, Nature Reviews, Drug Discovery, vol. 2, May 2003, pp. 347-360.

Duncan, Ruth, "Polymer Conjugates as Anticancer Nanomedicines," Nature Publishing Group, Nature Reviews, Cancer, vol. 6, Sep. 2006, pp. 688-701.

Hans, Meredith, et al., "Synthesis and Characterization of mPEG-PLA Prodrug Micelles," American Chemical Society, Biomacromolecules, vol. 6, Jul. 20, 2005, pp. 2708-2717.

Hanson, Jarrod A., et al., "Nonionic Block Copolypeptide Micelles Containing a Hydrophobic racemic-Leucine Core," National Institute of Health (NIH) Public Access-Author Manuscript, Macromolecules, Jul. 2010, vol. 43, No. 15, pp. 6268-6269.

Khandare, Jayant, et al., "Polymer-drug Conjugates: Progress in Polymeric Prodrugs," Elsevier Ltd, ScienceDirect, Progress in Polymer Science, vol. 31, 2006, pp. 359-397.

Maeda, H., et al., "Polymeric Drugs for Efficient Tumor-Targeted Drug Delivery Based on EPR-Effect," Elsevier B.V., ScienceDirect, European Journal of Pharmaceutics and Biopharmaceutics, vol. 71, 2009, pp. 409-419.

Matsumura, Yasuhiro, "Preclinical and Clinical Studies of NK012, and SN-38-incorporating Polymeric Micelles, which is Designed Based on EPR Effect," Elsevier B.V., ScienceDirect, Advanced Drug Delivery Reviews, vol. 63, 2011, pp. 184-192.

Maurer, Norbert, et al., "Developments in Liposomal Drug Delivery Systems," Emerging Biotherapeutic Technologies, Review, Ashley Publications, Ltd, Expert Opinion, Biol. Ther., vol. 1, No. 6, 2001, pp. 1-25.

Nallamothu, Ramakrishna, et al., "A Trageted Liposome Delivery System for Combretastatin A4: Formulation Optimization through Drug Loading and In Virto Release Studies," Research, PDA Journal of Pharmaceutical Science and Technology, vol. 60, No. 3, May-Jun. 2006, pp. 144-155.

Nallamothu, Ramakrishna, et al., "A Tumor Vasculature Targeted Liposome Delivery System for Combretastatin A4: Design, Characterization, and In Vitro Evaluation," AAPS PharmSciTech, vol. 7, No. 2, Article 32, 2006, pp. E1-E10.

Pasut, G., et al., "Polymer-drug Conjugation, Recent Achivements and General Strategies," Elsevier Ltd, Science Direct, Progress in Polymer Science, vol. 32, 2007, pp. 933-961.

Petrova, Svetlana, et al., "Synthesis of Amphiphilic [PEO(PCL)$_2$] Triarm Star-shaped Block Copolymers: A Promising System for in Cell Delivery," Springer Science+Business Media, LLC, vol. 23, Mar. 14, 2012, pp. 1225-1234.

Rodriguez, April R., et al., "Fine Tuning of Vesicle Assembly and Properties Using Dual Hydrophilic Triblock Copolypeptides," Wiley-VCH Verlag GmbH & Co. KGaA, Weinheim, Macromolecular Bioscience, vol. 12, 2012, pp. 805-811.

Rouf, Muhammad Abdur, et al., "Development and Characterization of Liposomal Fomulations for Rapamycin Delivery and Investigation of Their Antiproliferative Effect on MCF7 Cells," Informa UK Ltd., Journal of Liposome Research, vol. 19, No. 4, 2009, pp. 322-331.

Singer, Jack W., et al., "Poly-(L)-Glutamic Acid-Paclitaxel (CT-2103) [XYOTAX™], A Biodegradable Polymeric Drug Conjugate," Polymer Drugs in the Clinical Stage, Edited by Maeda et al., Kluwer Academic/Plenum Publishers, New York, 2003, pp. 81-99.

Van Domeselaar, Gary H., et al., "Application of Solid Phase Peptide Synthesis to Engineering PEO-peptide Block Copolymers for Drug Delivery," Elsevier Science B. V., ScienceDirect, Colloids and Surfaces B: Biointerfaces, vol. 30, 2003, pp. 323-334.

Forrest et al., "In vitro release of the mTOR inhibitor rapamycin from poly(ethyleneglycol)-b-poly(epsilon-caprolactone) micelles," Journal of Controlled Release, Elsevier, Amsterdam, NL, vol . 110, No. 2 , Jan. 10, 2006 (Jan. 10, 2006), pp. 370-377.

Chen et al., "Enantiomeric PLA-PEG block copolymers and their stereocomplex micelles used as rifampin delivery," Journal of Nanoparticle Research; An Interdisciplinary Forum for Nanoscale Science and Technology, Kluwer Academic Publishers, DO, vol. 9, No. 5, Jul. 28, 2006 (Jul. 28, 2006), pp. 777-785.

Lu et al., "Poly(ethyleneglycol)-block-poly(2-methyl-2-benzoxycarbonyl-propylene carbonate) micelles for rapamycin delivery: in vitro characterization and biodistribution," Journal of Pharmaceutical Sciences, vol. 100, No. 6, Jun. 24, 2011 (Jun. 24, 2011), pp. 2418-2429.

European search report dated Jul. 8, 2014 for Application EP 13195503 pp. 1-4.

* cited by examiner

USE OF UMIROLIMUS AND ITS DERIVATIVES FOR TREATING CANCER

CROSS-REFERENCE TO RELATED APPLICATIONS

The present application claims the benefit of U.S. Provisional Patent Application Ser. No. 61/732,629 filed on Dec. 3, 2012. The content of that application is hereby incorporated by reference in its entirety.

BACKGROUND

Tumors tend to develop resistance to chemotherapy drugs over time. To overcome such drug resistance, doctors routinely prescribe different chemotherapy drugs at different stages of treatment. Therefore, cancer patients will have a higher probability of surviving their particular cancer as the number of novel anti-cancer drugs increases.

Sirolimus, also known as rapamycin, is a lipophilic macrolide antibiotic initially developed for use as an immune suppressor for transplant patients. It was subsequently used in a drug coating for coronary artery stents, where it functions to reduce restenosis following angioplasty by inhibiting smooth muscle cell proliferation. Sirolimus also has anti-tumor activity. See U.S. Pat. No. 4,885,171.

Derivatives of sirolimus have also been found to be effective for treating certain cancers. For example, everolimus, a sirolimus derivative, is an approved drug for treating both advanced kidney cancer and inoperable progressive or metastatic pancreatic neuroendocrine tumors.

Umirolimus (40-alkoxyalkyl rapamycin or biolimus A9), a highly lipophilic derivative of sirolimus, is 10 times more lipophilic as compared to other "limus" family compounds such as sirolimus and everolimus. See J. Med. Chem. 2000, 43:2922-2928. This property gives umirolimus a higher affinity for lipid-rich cell membranes. However, such a high lipophilicity makes umirolimus less soluble in typical pharmaceutical preparations. Consequently, special formulations of umirolimus are needed to effectively deliver it to the site of a tumor.

The need exists for developing new chemotherapy agents containing umirolimus formulations which are soluble and stable in aqueous solution, have prolonged circulation after administration, and have tumor targeting capability.

SUMMARY

The main objective of the present invention is to provide umirolimus formulations for treating cancer. Thus, the main aspect of this invention relates to vehicle-encapsulated umirolimus or umirolimus conjugates.

Provided is a pharmaceutical formulation that includes umirolimus encapsulated in a liposome or a polymer micelle, together with a pharmaceutically acceptable excipient, carrier, or diluent.

Also provided is a method for treating cancer by administering to a subject an effective amount of the pharmaceutical formulation that includes umirolimus encapsulated in a liposome or a polymer micelle.

In another embodiment, a pharmaceutical formulation is provided that includes umirolimus conjugated to a polymer, together with a pharmaceutically acceptable excipient, carrier, or diluent.

In yet another embodiment, a method is provided for treating cancer by administering to a subject an effective amount of the pharmaceutical formulation that includes umirolimus conjugated to a polymer.

The details of one or more embodiments of the invention are set forth in the drawing and description below. Other features, objects, and advantages of the invention will be apparent from the description and from the claims. All references cited herein are hereby incorporated by reference in their entirety.

DETAILED DESCRIPTION

The main aspect of the invention relates to vehicle-encapsulated umirolimus formulations and umirolimus conjugate formulations for treating cancer.

In one embodiment, a pharmaceutical formulation is provided that includes umirolimus encapsulated in a liposome. The liposome includes a polyethylene glycol (PEG) conjugated phospholipid (PEGylated phospholipid) and a phosphatidylcholine (PC). The PEG has a length of 10-3000 monomeric units. In a preferred embodiment, the PEG has a length of 40-150 monomeric units. The umirolimus is present at a molar ratio of 0.1-10% based on the amounts of PEGylated phospholipid and PC.

The phospholipid can be, but is not limited to, distearoylphosphatidylcholine (DSPC), distearoylphosphatidylethanolamine (DSPE), distearoylphosphatidylglycerol (DSPG), dimyristoylphosphatidylcholine (DMPC), dioleoylphosphatidylcholine (DOPC), dioleoylphosphatidylethanolamine (DOPE), or dipalmitoylphosphatidylglycerol (DPPG). The PC can be, but is not limited to, hydrogenated soy PC (HSPC), egg PC, or soy PC.

In a preferred embodiment, the phospholipid is DSPE, the PC is HSPC, and a molar ratio between the umirolimus, the PEGylated phospholipid, and the PC is 10:60:30.

In an additional embodiment, the formulations described above also include cholesterol. For example, the formulation can include cholesterol, PEGylated DSPE, HSPC, and umirolimus at a molar ratio of 0.1-2%, where the molar ratio between the PEGylated DSPE, HSPC, and cholesterol is 55-65:2-10:20-40.

Also provided is a pharmaceutical formulation that includes umirolimus encapsulated in a polymer micelle. The umirolimus can be present at 5-40% by weight of the polymer micelle. The polymer can be a tri-arm block co-polymer or a block co-polymer.

The tri-arm block co-polymer can contain a hydrophilic polymer conjugated to two hydrophobic polymers. For example, the hydrophilic polymer can be PEG and the two hydrophobic polymers can both be polylactide (PLA), i.e., $PEG(PLA)_2$. In another embodiment, the hydrophilic polymer is PEG and the hydrophobic polymers are both polycaprolactone (PCL), i.e., $PEG(PCL)_2$.

The tri-arm block co-polymer can also contain a hydrophilic peptide conjugated to two hydrophobic polymers. For example, the hydrophilic peptide can be poly-Asp, poly-Gln, poly-Asn, or poly-Glu. The two hydrophobic polymers can both be PLA or PCL. The molecular weight of the hydrophobic polymer can be 1000-5000 Da. In a preferred embodiment, the hydrophobic polymer is PCL. The hydrophilic peptide can be 20-50 amino acids in length.

In another embodiment, the tri-arm block co-polymer contains a hydrophilic peptide conjugated to two hydrophobic peptides. The hydrophilic peptides can be poly-Asp, poly-Gln, poly-Asn, or poly-Glu. The hydrophobic peptides can be poly-Tyr, poly-Leu, poly-Phe, poly-Ala, or poly-Ile. The hydrophilic peptide can be 20-50 amino acids in length, and the hydrophobic peptide can be 5-40 amino acids in length. In a preferred embodiment, the hydrophobic peptide is poly-Ile or poly-Leu.

As mentioned above, the umirolimus can be encapsulated in a polymer micelle in which the polymer is a block co-polymer. The umirolimus can be present at 5-40% by weight of the polymer micelle.

The block co-polymer can contain a hydrophilic polymer conjugated to a hydrophobic polymer. For example, the hydrophilic polymer can be PEG and the hydrophobic polymer can be PLA, i.e., PEG-PLA. In another embodiment, the hydrophilic polymer is PEG and the hydrophobic polymer is PCL, i.e., PEG-PCL. The PEG can have a length of 10-3000 monomeric units. The molecular weight of the hydrophobic polymers PLA and PCL can be 1000-10000 Da.

Alternatively, the block co-polymer can contain a hydrophilic peptide conjugated to a hydrophobic peptide or a hydrophobic peptide conjugated to a hydrophilic polymer.

For example, the block co-polymer can contain the hydrophilic peptide poly-Asp, poly-Gln, poly-Asn, or poly-Glu. The hydrophobic peptide can be poly-Ala, poly-Leu, poly-Ile, poly-Val, poly-Phe, poly-Tyr, or poly-Trp. The hydrophobic peptide can be 10-40 amino acids in length, while the hydrophilic peptide can be 40-300 amino acids in length.

Any of the above amino acid residues making up the hydrophobic and hydrophilic peptides can be an L amino acid or a D amino acid. In other embodiments, a racemic mixture (rac) of the above-mentioned amino acids can be used. In an embodiment, the block co-polymer contains the hydrophilic peptide poly-rac-Asp and the hydrophobic peptide poly-rac-Phe. In another embodiment, the hydrophobic peptide is 10-40 amino acids in length and the hydrophilic peptide is 40-300 amino acids in length.

In yet another embodiment, the umirolimus is encapsulated in a polymer micelle that includes a block co-polymer containing a hydrophobic peptide conjugated to a hydrophilic polymer. The hydrophobic peptide can be 5-40 amino acids in length, and the hydrophilic polymer can have a molecular weight of 2,000-100,000 Dal.

The hydrophobic peptide can be, for example, poly-Tyr, poly-Leu, poly-Ala, poly-Ile, poly-Val, or poly-Phe. In preferred embodiments, the hydrophobic peptide is poly-Leu or poly-Ile. The hydrophilic polymer can be PEG.

Also provided is a pharmaceutical formulation that includes umirolimus conjugated to a polymer. The umirolimus can be present at 10% to 50% by weight of the polymer conjugate. The molecular weight of the polymer is in the range of 20,000 Dal to 100,000 Dal. The polymer can be, but is not limited to, poly-Glu, poly-Asp, poly-Lys, poly-Tyr, and PEG. In additional embodiments, the PEG is a 4-arm or 8-arm branched polymer. In a preferred embodiment, the PEG is a 4-arm branched polymer.

In another embodiment, umirolimus can be conjugated to a block co-polymer that includes a hydrophobic polymer and a hydrophilic polymer, where the umirolimus is bonded to the hydrophobic polymer. The hydrophobic polymer can be PLA, PCL, or a hydrophobic peptide. The hydrophilic polymer can be PEG.

In embodiments where the hydrophobic polymer is a hydrophobic peptide, the hydrophobic peptide can be poly-Ala, poly-Leu, poly-Ile, poly-Val, poly-Phe, poly-Tyr, or poly-Trp.

Any of the above-mentioned umirolimus-containing formulations can be used to produce a medicament for treating cancer.

The current invention provides a method for treating cancer by administering to a subject an effective amount of the pharmaceutical formulations described above that include encapsulated umirolimus or umirolimus conjugates.

For example, a pharmaceutical formulation including umirolimus encapsulated in a liposome can be administered to a cancer patient via any conventional method, including, but not limited to, intraperitoneal injection, intravenous injection, direct injection into a tumor, injection into the arterial circulation upstream of a tumor, and nasal inhalation. The pharmaceutical formulations described above can also be administered orally in pill form or in capsule form.

Not to be bound by theory, it is believed that (i) umirolimus, a lipid soluble drug, is stabilized in the lipid bilayer of a liposome, (ii) umirolimus loaded into liposomes is released slowly and continuously after administration, and (iii) encapsulation provides higher aqueous solubility and stability to umirolimus as compared to pure umirolimus.

In another embodiment, a pharmaceutical formulation including umirolimus encapsulated in a polymer micelle can be administered to a cancer patient via the above-described methods, including, but not limited to, intraperitoneal injection, intravenous injection, direct injection into a tumor, injection into the arterial circulation upstream of a tumor, and nasal inhalation.

Both liposome and micelle encapsulated drug delivery advantageously exhibit passive disease-site targeting. Umirolimus delivered in encapsulated form would tend to accumulate at sites of a tumor, an infection, or an inflammation, where these sites have a larger than normal porous microvascular structure.

In yet another embodiment, a method is provided for treating cancer by administering to a subject an effective amount of the above-described pharmaceutical formulations that include umirolimus conjugated to a polymer.

Formulations including conjugated umirolimus, similar to the encapsulated umirolimus formulations described above, can be administered to a subject by conventional means, including, but not limited to, intraperitoneal injection, intravenous injection, direct injection into a tumor, injection into the arterial circulation upstream of a tumor, and nasal inhalation.

Conjugated umirolimus would act as a prodrug. More specifically, umirolimus would be released from an umirolimus/polymer conjugate by hydrolysis in body tissues after administration of the conjugate.

Umirolimus-polymer conjugates, as compared to pure umirolimus, are expected to demonstrate increased water solubility, enhanced drug stability, prolonged drug circulation time in the blood, increased tumor vascular permeability for tumor targeting (an EPR effect), and improved pharmacokinetics.

The types of cancer that can be treated by administering the above-described formulations include but are not limited to acute lymphocytic leukemia, acute myeloid leukemia, adrenal cancer, adult soft tissue sarcoma, anal cancer, aplastic anemia, basal and squamous cell skin cancer, bile duct cancer, bladder cancer, bone cancer, brain/CNS tumors, breast cancer, breast cancer in man, cancer in children, cancer of unknown primary, Castleman's disease, cervical cancer, chronic lymphocytic leukemia, chronic myeloid leukemia, chronic myelomonocytic leukemia, colorectal cancer, endometrial cancer, esophagus cancer, Ewing Family of tumors, eye cancer, gallbladder cancer, gastric cancer, gastrointestinal carcinoid, gastrointestinal stromal tumor, gestational trophoblastic disease, Hodgkin's disease, Kaposi's sarcoma, kidney cancer, laryngeal and hypopharyngeal cancer, leukemia in children, liver cancer, lung cancer-non small cell, lung cancer-small cell, Lung carcinoid tumor, malignant mesothelioma, melanoma skin cancer, multiple myeloma, myelodysplastic syndrome, nasal cavity and paranasal sinus cancer, nasopharyngeal cancer, neuroblastoma, non-Hodgkin's lymphoma, oral cavity and oropharangeal cancer, osteosarcoma, ovarian cancer, pancreatic cancer, penile cancer, pituitary tumors, prostate cancer, renal cell carcinoma, retinoblastoma, rhabdomyosarcoma, salivary gland cancer, skin lymphoma, small intestine cancer, stomach cancer, testicular cancer, thymus cancer, thyroid cancer, uterine sarcoma, vaginal cancer, vulvar cancer, Waldenstrom's macroglobulinemia, and Wilms' tumor.

Without further elaboration, it is believed that one skilled in the art can, based on the description above, utilize the present invention to its fullest extent. The specific examples below are to be construed as merely illustrative, and not limitative of the remainder of the disclosure in any way whatsoever.

EXAMPLE 1

Umirolimus Inhibits Cancer Cell Growth

Umirolimus was added to cultured cell lines derived from 9 types of human cancer. After 72 hours of in vitro culture, the 50% inhibitory concentration ($IC_{50}$) of umirolimus on cell growth was measured using the CellTiter-Glo luminescent cell viability assay.

TABLE 1

Inhibition of cancer cell growth by umirolimus

| Cell line/human cancer type | $IC_{50}$ (μM) | Maximum inhibition (%) |
|---|---|---|
| SNU-16/gastric | 1.14 | 99.75 |
| BxPC-3/pancreatic | 3.07 | 77.24 |
| AZ-521/gastric | 4.23 | 99.88 |
| RPMI-8226/multiple myeloma | 6.8 | 99.26 |
| NCI-H460/lung | 7.07 | 88.99 |
| A2780/ovarian | 7.31 | 100.19 |
| SK-HEP-1/liver | 7.81 | 99.97 |
| K562/chronic myelogenous leukemia | 7.97 | 98.49 |
| SK-MES-1/lung | 8.24 | 96.57 |
| SW620/colorectal | 8.33 | 55.69 |
| MDA-MB-231/breast | 9.52 | 99.23 |

The results indicated that 11 cell lines from 9 types of human cancers are sensitive to umirolimus with an $IC_{50}$ less than 10 μM.

EXAMPLE 2

Figure 1:
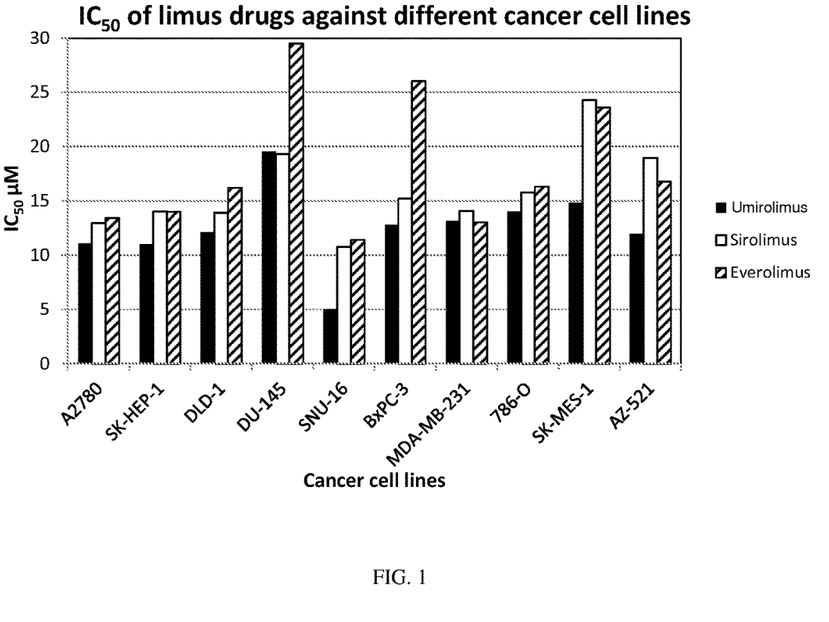
FIG. 1 is a plot of 50% inhibitory concentration ($IC_{50}$) values for three "limus" drugs tested on various exemplary human cancer cell lines.

Inhibition of Cancer Cell Growth by Umirolimus as Compared to Sirolimus and Everolimus The $IC_{50}$ for 3 "limus" drugs for inhibiting the growth of 10 human cancer cell is lines was measured using the CellTiter-Glo luminescent cell viability assay as described in Example 1. The ten exemplary human cancer cell lines tested were SK-MES-1 (lung cancer), BxPC-3 (pancreatic cancer), AZ-521 (gastric cancer), SNU-16 (gastric cancer), SK-HEP-1 (liver cancer), A2780 (ovarian cancer), MDA-MB-231 (breast cancer), DLD-1 (colorectal cancer), DU-145 (prostate cancer) and 786-O (kidney cancer). The results are shown in FIG. 1.

The $IC_{50}$ of umirolimus was unexpectedly superior to that of sirolimus and everolimus for 8 out of the 10 cancer cell lines tested. More specifically, umirolimus was superior in inhibiting the growth of the following cell lines: A2780, SK-HEP-1, DLD-1, SNU-16, BxPC-3, 786-O, SK-MES-1, and AZ-521.

EXAMPLE 3

Umirolimus-Containing Liposome

Umirolimus (0.1-2 mM of umirolimus/100 mM total lipid), PEGylated distearoyl phosphatidyl ethanolamine (mPEG-DSPE; polyethylene glycol monomer chain length of 2,000), hydrogenated soy phosphatidylcholine (HSPC), and cholesterol (DSPE/HSPC/cholesterol ratio: 55-65/2-10/20-40) are dissolved in ethanol (10-30% of total volume of liposome). The mixture is then injected into 10 mL of distilled water with constant stirring. The liposome solution thus formed is extruded 10 times through a 0.5 μm polycarbonate filter and then 10 times through a 0.22 μm polycarbonate filter to reduce the particle size to 100-200 nm.

EXAMPLE 4

Umirolimus-Containing Liposome Without Cholesterol

Umirolimus, mPEG-DSPE (polyethylene glycol monomer chain length of 2,000), and HSPC, (umirolimus/DSPE/HSPC ratio: 10-30/60-80/10-20) are dissolved in ethanol (10-30% of total volume of liposome). The mixture is then injected into 10 mL of distilled water with constant stifling. The liposome solution thus formed is extruded 10 times through a 0.5 μm polycarbonate filter and then 10 times through a 0.22 μm polycarbonate filter to reduce the particle size to 100-200 nm.

EXAMPLE 5

Umirolimus-Containing Tri-Arm Block Co-Polymer Micelle

First methyl PEG-OH is reacted with 4-(chloromethyl)-2,2-dimethyl-1,3-dioxolane to form a ketal derivative. Following the removal of the ketal group in an acidic solution, the resulting diol is used for lactide polymerization to obtain a $PEG(PLA)_2$ tri-arm block co-polymer.

Fifty milligrams of the $PEG(PLA)_2$ tri-arm block co-polymer and 5-20 mg of umirolimus are dissolved in 2.0 mL of acetonitrile. The acetonitrile is then removed using a rotary evaporator. The resulting polymer film is hydrated with 2.0 mL of water to form micelles. The solution of umirolimus-containing $PEG(PLA)_2$ micelles is filtered through a 0.22 μm filter to sterilize it before use.

EXAMPLE 6

Umirolimus-Containing Peptide-Based Tri-Arm Block Co-Polymer Micelle

First, a hydrophobic peptide of 5-40 amino acids in length is synthesized by solid phase peptide synthesis (SPPS) using an automated peptide synthesizer on Rink amide methyl-benzhydrylamine (MBHA) resin using standard Fmoc/t-Butyl protected amino acids and O-7 azabenzotriazol tetramethyluronium hexafluorophospahate (HATU) active-ester based coupling. The synthesized peptides can be poly-Tyr, poly-Leu, poly-Ala, poly-Ile, poly-Val, or poly-Phe.

Second, a hydrophilic peptide of 20-50 amino acids in length terminating in a lysine residue is also synthesized by solid phase peptide synthesis as described above. The synthesized peptides can be poly-Asp, poly-Gln, poly-Asn, or poly-Glu. The two active amine groups in the terminal lysine are each used for conjugating to the hydrophobic polypeptide described above utilizing HATU as the coupling reagent. Protecting groups on the peptide side chains are removed by treatment with 95% trifluoroacetic acid (TFA) and the peptide-based tri-arm block co-polymer is obtained by methanol precipitation.

50 mg of the peptide-based tri-arm block co-polymer and 5-20 mg of umirolimus are dissolved in 2.0 mL of acetonitrile. The acetonitrile is then removed using a rotary evaporator. The resulting film is hydrated with 2.0 mL of water to form micelles. The solution of umirolimus-containing micelles is filtered through a 0.22 µm filter to sterilize it before use.

EXAMPLE 7

Umirolimus-Containing Peptide/Polymer-Based Tri-Arm Block Co-Polymer Micelle

A hydrophilic peptide of 20-50 amino acids in length terminating in a lysine residue is synthesized by solid phase peptide synthesis as described above in Example 5. The synthesized peptides can be poly-Asp, poly-Gln, poly-Asn, or poly-Glu. The two active amine groups in the terminal lysine are each used for polylactide (PLA) synthesis as described above in Example 4. Polycaprolactone (PCL) can also be synthesized instead of the polylactide.

Protecting groups on the peptide side chains are removed by treatment with 95% TFA and the peptide-(PLA)$_2$ or peptide-(PCL)$_2$ tri-arm block co-polymer is obtained by methanol precipitation.

50 mg of peptide/polymer tri-arm block co-polymer and 5-20 mg of umirolimus are dissolved in 2.0 mL of acetonitrile. The acetonitrile is then removed using a rotary evaporator. The resulting film is hydrated with 2.0 mL of water to form micelles. The solution of umirolimus-containing peptide/polymer micelles is filtered through a 0.22 µm filter to sterilize it before use.

EXAMPLE 8

Umirolimus-Containing Peptide/Polymer-Based Block Co-Polymer Micelle

Peptides of 5-40 residues in length containing hydrophobic amino acids are synthesized by SPPS using an automated peptide synthesizer on Rink amide MBHA resin using standard Fmoc/t-Butyl protected amino acids and HATU active-ester based coupling. The hydrophobic peptide can be polyAla, polyIle, polyVal, or polyTrp. Both levo and racemic amino acids can be used.

To form a peptide/polymer block co-polymer, the hydrophobic peptide is attached to α-methyl-ω-proprionic acid-poly(ethylene oxide) (PEO—OCH$_2$CH$_2$—COOH) by solution phase condensation. The molecular weight of the PEO is in the range of 2,000-100,000 Dal.

50 mg of peptide/polymer block co-polymer and 5-20 mg of umirolimus are dissolved in 2.0 mL of acetonitrile. The acetonitrile is then removed using a rotary evaporator. The resulting film is hydrated with 2.0 mL of water to form micelles. The solution of umirolimus-containing peptide/polymer micelles is filtered through a 0.22 µm filter to sterilize it before use.

EXAMPLE 9

Umirolimus-Containing Peptide Micelle Including Hydrophilic and Hydrophobic Peptide Domains A hydrophobic peptide is purchased or synthesized by N-carboxyanhydride (NCA) polymerization to serve as a macroinitiator. A hydrophilic peptide is then assembled by adding the macroinitiator into a solution of dichloromethane containing the desired amino acid-NCA conjugates. The reaction is carried out at 40° C. for 24 h under an Ar atmosphere. The reaction mixture is poured into cooled methanol, causing the precipitation of a white solid product. The product is characterized by NMR and gel permeation chromatography. The removal of amino acid side chain protecting groups is carried out by treatment of the product with 95% TFA in water. The deprotection reaction mixture is poured into cooled diethyl ether to precipitate a white solid polymer. The resulting hydrophilic-hydrophobic peptide block polymer is dried under vacuum and characterized by NMR.

50 mg of hydrophilic-hydrophobic peptide block co-polymer and 5-20 mg of umirolimus are dissolved in 2.0 mL of acetonitrile. The acetonitrile is then removed using a rotary evaporator. The resulting peptide polymer film is hydrated with 2.0 mL of water to form micelles. The solution of umirolimus-containing peptide micelle is filtered through a 0.22 µm filter to sterilize it before use.

EXAMPLE 10

Umirolimus-Polymer Micelle Prodrug Conjugate mPEG-PLA-COOH co-polymer is synthesized by ring-opening polymerization. Briefly, lactide and 2 mol % α-methyl-ω-proprionic acid-PEO (PEO—OCH2CH2—COOH) are dissolved at 160° C. under nitrogen. 0.2% stannous 2-ethylhexanoate was added and the reaction carried out under vacuum at a temperature of 140° C. for 90 min. The co-polymer thus formed is then dissolved in dichloromethane and precipitated in cold ether.

The mPEG-PLA co-polymer (1000 g) and umirolimus (50 mg) are dissolved in anhydrous DCM. 20 mg 4-dimethyl aminopyridine, 70 mg bromotripyrrolidino phosphonium hexafluorophosphate, and 50 µL diisopropyl ethylamine (DIPEA) are then added. The reaction is stirred for 24 h at room temperature followed by complete removal of the solvent by rotary evaporation. The resulting co-polymer/drug conjugate is washed with an excess of ethanol to remove unreacted umirolimus and catalysts. The prodrug structure and degree of conjugation are determined by dissolving the conjugate polymer in deuterated dimethylsulfoxide and analyzing it by $^1$H and $^{13}$C NMR.

EXAMPLE 11

Umirolimus Conjugated to a Hydrophilic Polypeptide

A mixture of 100 mg of poly-glutamic acid (MW>50,000), 50 mg of umirolimus, and 20 µL of DIPEA in 3.5 mL of dry dimethylformamide was cooled to 0° C. 30 mg of dicyclohexylcarbodiimide was added and the reaction was incubated at room temperature overnight. The mixture was poured into chloroform to stop the reaction and to precipitate the umirolimus/peptide conjugate. The resulting precipitate was further washed with chloroform several times to obtain a white powder.

EXAMPLE 12

Umirolimus Encapsulated in a PEG-PLA Block Copolymer

A mixture of 23.42 mg of PEG-PLA block copolymer was dissolved together with 2.23 mg of umirolimus in 0.5 mL of dichloromethane. The dichloromethane was evaporated in a laminar flow hood at room temperature. The polymer film thus formed was rehydrated in 2.2 mL of HPLC grade H$_2$O. The resulting solution was filtered through a polytetrafluoroethylene (PTFE) membrane having a pore size of 0.22 µm.

EXAMPLE 13

Umirolimus Encapsulated in a PEG-PCL Block Copolymer

A mixture of 33.24 mg of PEG-PCL block copolymer was dissolved together with 3.17 mg of umirolimus in 0.5 mL of dichloromethane. The dichloromethane was evaporated in a laminar flow hood at room temperature. The polymer film thus formed was rehydrated in 4.0 mL of HPLC grade H$_2$O. The resulting solution was filtered through a PTFE membrane having a pore size of 0.22 µm.

EXAMPLE 14

Physical Properties of Block Copolymer Polymer-Encapsulated Umirolimus

Solubility

The solubility of umirolimus in H$_2$O was determined and compared to the solubility in H$_2$O of umirolimus encapsulated in PEG-PLA and PEG-PCL described, respectively, in Example 12 and Example 13 above. HPLC was used to measure the umirolimus concentration after dissolving the drug or encapsulated drug. The results are shown in Table 2 below. Pure umirolimus had a solubility of 0.11 µg/mL in water. The solubility of umirolimus was lower than that of sirolimus (2.6 µg/mL) reported in the literature. Umirolimus encapsulated in PEG-PCL and PEG-PLA had a solubility of 55.6 g/mL and 739.1 g/mL, respectively.

TABLE 2

Water solubility of umirolimus preparations

|  | Solubility (µg/mL) | Fold increase |
| --- | --- | --- |
| umirolimus | 0.11 | 1 |
| umirolimus + PEG-PCL | 55.6 | 505 |
| umirolimus + PEG-PLA | 739.1 | 6719 |

Stability

Figure 2A:
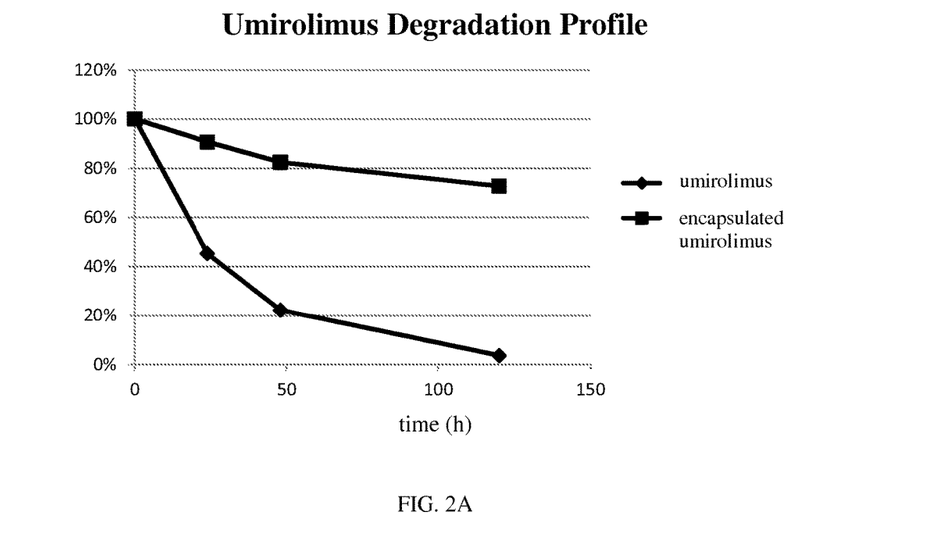
FIG. 2A is a plot of percentage of umirolimus or encapsulated umirolimus remaining versus time.

The stability of umirolimus was compared to that of umirolimus encapsulated in a PEG-PLA block copolymer micelle as described in Example 12 above. Solutions of umirolimus (50 µg/mL) and encapsulated umirolimus (157.4 µg/mL) in 90% PBS, 10% MeOH were placed in water bath at 37° C. The stability of the umirolimus was determined by measuring the drug content at different incubation times. The results are shown in FIG. 2A. Umirolimus encapsulated in a PEG-PLA block copolymer micelle was significantly more stable than the unencapsulated drug.

The half-life of umirolimus was calculated based on the following equation:

$$\text{half-life} = (t \cdot \ln(2))/(LN(C_t/C_{t0})),$$

where t is the end time point, $C_t$ is the concentration at the end time point, and $C_{t0}$ is the initial concentration. The results indicated that the half-life of umirolimus was 21 h, while the half-life of umirolimus encapsulated in the PEG-PLA block copolymer micelle was 148 h, representing a 7-fold increase.

Release Profile

Figure 2B:
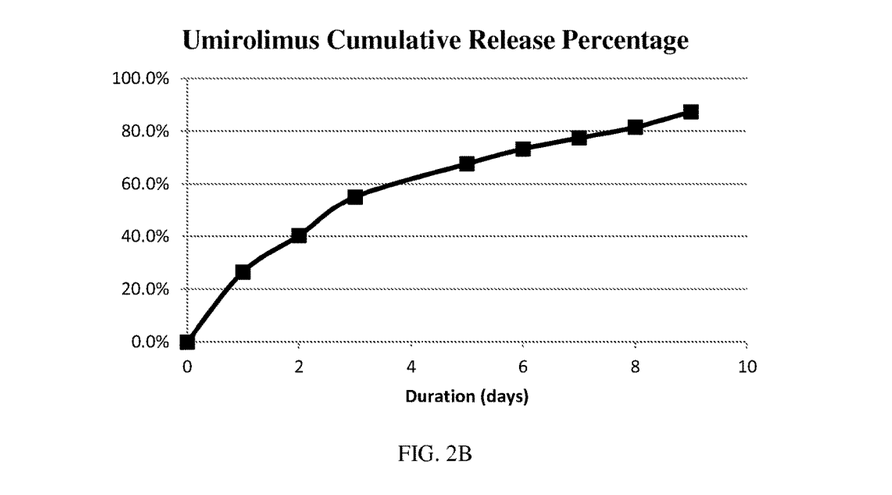
FIG. 2B is a plot of percentage of umirolimus released from a polymer micelle versus time.

The cumulative drug release profile of umirolimus encapsulated in PEG-PLA block copolymer micelles was determined. The polymer micelles (380 µg) were suspended in 5 mL of a 90% PBS/10% methanol solution. The suspension was incubated in a water bath at 37° C. At each time point, 0.2 mL of the suspension was transferred to a microcentrifuge tube. The polymer micelles in the tube were collected by centrifugation at 15,000×g for 15 min. at 5° C. After removal of the supernatant, the resulting pellet was resuspended by sonication in 0.2 mL fresh methanol. The resulting solution was analyzed by HPLC to determine the amount of umirolimus remaining in the polymer micelles. The results are shown in FIG. 2B. Approximately 80% of the umirolimus is released within 8 days of incubation.

EXAMPLE 15

In Vivo Inhibitory Efficacy Study

The SNU-16 human gastric cancer xenograft model in BALB/c nude mice was employed to evaluate the inhibitory efficacy of encapsulated umirolimus,.

SNU-16 tumor cells were cultured in suspension in RPMI-1640 medium supplemented with 10% heat inactivated fetal bovine serum at 37° C. in 5% CO$_2$. Cells are routinely subcultured twice weekly. Cells in the exponential growth phase were harvested and counted prior to inoculating them into Nu/nu mice to establish a tumor.

Each mouse was inoculated subcutaneously in the upper right back with 1×10$^7$ SNU-16 cells in 0.1 mL of PBS together with matrigel (1:1) to support tumor development. The drug or vehicle treatments were initiated when the mean tumor size reaches approximately 150 mm$^3$ on day 8 after injection. Each animal was injected intraperitoneally for 5 consecutive days beginning at day 8. The formulation administered and the numbers of animals in each study group are shown in Table 3 below.

TABLE 3

| | | | Dose | Dosing | |
|---|---|---|---|---|---|
| Compounds | N | Preparation | (mg/kg) | Route | Schedule |
| Vehicle (Group 1) | 10 | Add 2.0 mL of sterile 8% ethanol and 2.0 ml of sterile 10% polysorbate 80 to a 5 ml glass vial, vortex to form a clear solution. | 0 | i.p. | QD x 5 |
| PEG-PLA Encapsulated Umirolimus (Group 2) | 10 | Measure 70 mg test compound (4.5 mg drug equivalent after filtration) in a 10 mL glass vial, add 6 mL injection water, and vortex/sonicate until the test compound is fully suspended in solution and no precipitate is observed. The resulting solution is then filtered through a 0.45 micron filter (23 mm or 40 mm, PDVF or PTFE) to produce a 0.75 mg/mL nano-suspension. | 15 | i.p. | QD x 5 |

After tumor cell inoculation, the animals were checked daily for morbidity and mortality. At the time of routine monitoring, the animals were checked for any effects of tumor burden and treatments on normal behavior, e.g., mobility, visual estimation of food and water consumption, body weight gain/loss, eye matting, and any other abnormal effect. Death and observed clinical signs were recorded for each animal.

Tumor volumes were measured twice weekly in two dimensions using a caliper, and the volume calculated using the formula: $V=0.5 \: a \times b^2$, where a and b are the long and short diameters of the tumor, respectively.

Figure 3:
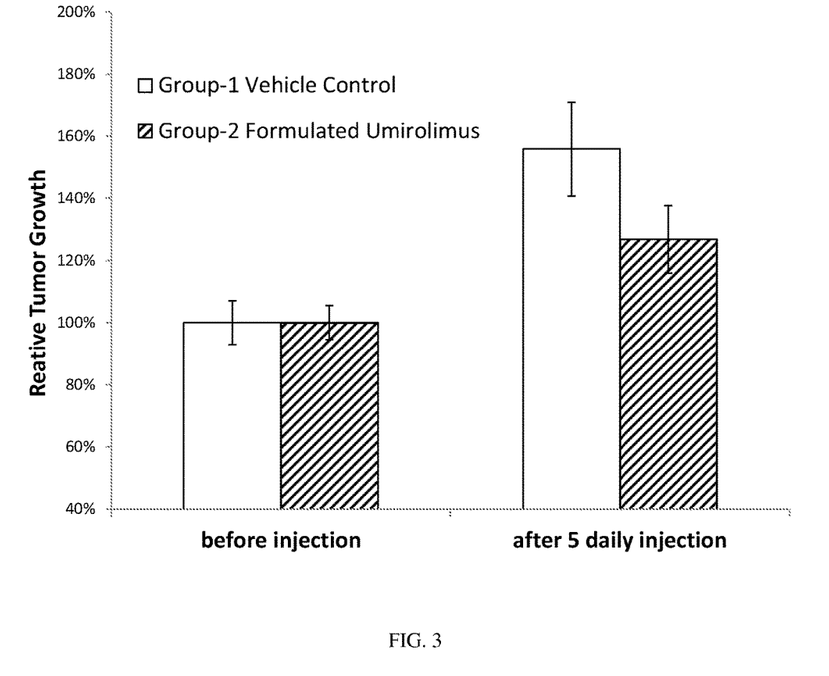
FIG. 3 is a bar graph showing the reduction of tumor growth in experimental animals after injection of encapsulated umirolimus.

The results are shown in FIG. 3. Umirolimus encapsulated in a PEG-PLA block copolymer micelle was effective for slowing the growth of experimental tumors.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A pharmaceutical formulation for treating cancer, the formulation comprising umirolimus encapsulated in a polymer micelle, and a pharmaceutically acceptable excipient, carrier, or diluent, wherein the polymer micelle includes a di-block co-polymer, the di-block co-polymer being polyethyleneglycol-polylactide (PEG-PLA) or polyethyleneglycol-polycaprolactone (PEG-PCL), the PEG has a molecular weight of 2000 Da, the molecular weights of the PLA and PCL are each 1000-10000 Da, the polymer micelle has a particle size of 10-200 nm, the umirolimus is present at 5-40% by weight of the polymer micelle, and the umirolimus is the only drug in the formulation.

2. The formulation of claim 1, wherein the di-block co-polymer is PEG-PLA having a molecular weight of 1000 to 5000 Da.

3. The formulation of claim 1, wherein the di-block co-polymer is PEG-PCL having a molecular weight of 1000 to 5000 Da.

* * * * *